(12) United States Patent
Bourdon et al.

(10) Patent No.: US 10,132,734 B2
(45) Date of Patent: Nov. 20, 2018

(54) PROCESS FOR EVALUATING THE MECHANICAL PERFORMANCE OF A FILLER GEL

(71) Applicant: TEOXANE, Geneva (CH)

(72) Inventors: Francois Bourdon, Gaillard (FR); Stephane Meunier, Thoiry (FR)

(73) Assignee: TEOXANE, Geneva (CH)

( * ) Notice: Subject to any disclaimer, the term of this patent is extended or adjusted under 35 U.S.C. 154(b) by 0 days.

(21) Appl. No.: 15/560,547

(22) PCT Filed: Mar. 22, 2016

(86) PCT No.: PCT/EP2016/056277
§ 371 (c)(1),
(2) Date: Sep. 22, 2017

(87) PCT Pub. No.: WO2016/150974
PCT Pub. Date: Sep. 29, 2016

(65) Prior Publication Data
US 2018/0120211 A1 May 3, 2018

(30) Foreign Application Priority Data
Mar. 24, 2015 (FR) ...................... 15 52449

(51) Int. Cl.
*G01N 11/00* (2006.01)
*C08B 1/00* (2006.01)
*A61K 31/00* (2006.01)
*A61K 8/04* (2006.01)
(Continued)

(52) U.S. Cl.
CPC .............. *G01N 11/00* (2013.01); *A61K 8/042* (2013.01); *A61K 8/735* (2013.01); *A61Q 19/08* (2013.01); *A61K 2800/91* (2013.01); *G01N 2011/0026* (2013.01)

(58) Field of Classification Search
CPC .......... A61K 8/00; A61Q 19/08; G01N 11/00; G01N 2011/0026
See application file for complete search history.

(56) References Cited

U.S. PATENT DOCUMENTS

2007/0184087 A1 8/2007 Voigts et al.
2011/0036151 A1 2/2011 Andle et al.
2011/0117041 A1 5/2011 Chantal et al.
(Continued)

FOREIGN PATENT DOCUMENTS

WO 2014064632 A1 5/2014

OTHER PUBLICATIONS

A. Magnin and J. M. Piau, "Shear Rheometry of Fluids With a Yield Stress", Journal of Non-Newtonian Fluid Mechanics, 23 (1987) 91-106.
(Continued)

*Primary Examiner* — Daniel S Larkin
(74) *Attorney, Agent, or Firm* — Shumaker, Loop & Kendrick, LLP (57) ABSTRACT

Process for evaluating the mechanical performance of a filler gel, comprising the step consisting in subjecting a sample of this gel to oscillating mechanical stresses making it possible to determine the elastic modulus G' and to deliver a score representative of the integration of G' over the stress and/or the deformation strain within a stress and/or strain interval that includes values of the modulus G' encountered beyond the linear viscoelasticity plateau.

8 Claims, 8 Drawing Sheets

(51) Int. Cl.
*A61K 8/73* (2006.01)
*A61Q 19/08* (2006.01)

(56) References Cited

U.S. PATENT DOCUMENTS

2013/0237615 A1 9/2013 Meunier et al.
2013/0253855 A1 9/2013 He et al.

OTHER PUBLICATIONS

A. Magnin and J. M. Piau, "Cone-and-Plate Rheometry of Yield Stress Fluids. Study of an Aqueous Gel", Journal of Non-Newtonian Fluid Mechanics, 36 (1990) 85-108.
International Search Report for PCT/EP2016/056277 dated Jun. 30, 2016 (4 pages).
Written Opinion for PCT/EP2016/056277 dated Jun. 30, 2016 (7 pages).

Fig. 15

PROCESS FOR EVALUATING THE MECHANICAL PERFORMANCE OF A FILLER GEL

BACKGROUND OF THE INVENTION

The present invention relates to the filler gels used in cosmetic surgery for filling wrinkles.

Such gels are, for example, based on hyaluronic acid and are injected under the skin using a syringe.

It is important for the gel to be able to be injected easily using a syringe equipped with a fine needle, and for the implant thus injected to be able to be positioned in a suitable manner in the injection site according to the stresses applied by the practitioner, and then to adapt to the stresses and dynamics of the face.

The rheology of the gel is therefore an essential element that it is advisable to control if it is sought to obtain optimal results.

The rheological quantities of the gels that are customarily most used are the elastic modulus G' and viscous modulus G", the phase angle $\delta$ being connected to these quantities (tan $\delta$=G"/G'). These data are obtained in oscillatory rheology and are normally measured for low oscillation stresses and amplitudes, i.e. in the linear viscoelasticity zone, where G', G" and $\delta$ are relatively constant; such a measurement does not reflect all of the mechanical stresses and deformations to which a filler gel is subjected depending on its function.

Attempts to use rheological measurements have to date not proved sufficiently predictive, and there is consequently a need to resolve this problem.

There is furthermore an advantage in having tools for characterizing and selecting gels in the laboratory, making it possible to avoid resorting to in vivo tests at the selection stage in the development of a product.

There is consequently a need to facilitate the development of a novel filler gel and in particular to be able to easily differentiate several gels in order to retain that or those having the most advantageous properties with respect to the desired result.

SUMMARY OF THE INVENTION

The invention achieves this objective owing to a process for evaluating the mechanical performance of a filler gel, comprising the step of subjecting a sample of this gel to oscillating mechanical stresses making it possible to determine the elastic modulus G' and to deliver a score representative of the integration of G' over the stress and/or the deformation strain within a stress and/or deformation strain interval that includes values of the modulus G' encountered beyond the linear viscoelasticity plateau. The integration interval is wide enough to include values of the modulus G' encountered beyond the linear viscoelasticity plateau. The lower limit of the integration interval is preferably taken, for the lowest stress and/or deformation strain values of the measurement, within the linear viscoelasticity range of the modulus G'.

Accordingly, the score is derived from the integration of G' over the stress and/or the deformation strain within a stress and/or deformation strain interval that includes values of the modulus G' encountered beyond the linear viscoelasticity plateau.

Knowledge of the G' integration score based on the integration of the modulus G' proves to be invaluable for comparing several gels and thus facilitating the selection thereof as a function of the applications.

For example, for an application of filling deep wrinkles or particularly atrophied regions of the face, it is advisable to choose the gels having a high integration score, whereas those having a lower score could suffice for moderate or fine facial wrinkles.

The integration may be a single integration and may be carried out over the stress, or as a variant over the deformation strain. The integration may also be a double integration and may be carried out over the stress and the deformation strain.

The integration interval may have, as upper limit, the deformation strain and/or stress values taken at a point where the modulus G' has decreased relative to its value in linear regime, in particular any point in the range of decrease of G' between the end of the plateau and the crossover. The upper limit corresponds for example to a decrease of at least 10% of the modulus G' relative to its average value over the plateau (linear viscoelasticity range). The upper limit is advantageously taken at the crossover point.

Preferably, a complementary creep measurement is also carried out. This measurement makes it possible to differentiate gels for which the G' integration scores are similar, having clinical performances and resistance to degradation performances which are quite similar. The gel which has a significantly higher slope of the creep offers the advantage of being more easily injectable and malleable, may improve the comfort of the patient and give a more natural effect by adapting to the dynamics of the face.

Thus, taking into account both the G' integration score and the creep gives information on the behaviour of the gel not only in situ, especially in terms of durability, firmness and mechanical power, but also on its behaviour in the positioning situation, especially in terms of placement of the implant during the injection, and of deformation forced by the dynamics of the face.

The process according to invention may be implemented with the aid of a rheometer and a rheometer control unit having computational means, so as to calculate the G' integration score and, where appropriate, the slope of the creep.

Information representative of the G' integration score may be printed or displayed on an information medium, in particular a notice, a packaging of the gel, an information or advertising panel, a commercial or medical brochure, a television screen or mobile telephone screen. This may give information on the performances of the gel. Where appropriate, information representative of the slope of the creep may also be printed or displayed, for example alongside the information representative of the G' integration score.

Another subject of the invention is a process for classifying the mechanical performances of a set of filler gels, in which the evaluation process as defined above is implemented for each of the gels of the set, and the gels are classified as a function of the results from the implementation of the evaluation process.

Another subject of the invention is a process for selecting a filler gel, in which the evaluation process as defined above is implemented for a set of gels to be tested, and the gel is selected as a function of the G' integration score. Use is also made, advantageously, of the creep measurement in order to differentiate gels for which the G' integration scores are similar.

Another subject of the invention is a process for manufacturing a filler gel, in which several candidate gels are manufactured in a small amount, one gel at least is selected on the basis of the results of the above selection process, and the selected gel is manufactured in an amount greater than that of the candidate gels, with a view to a commercial use.

Another subject of the invention is a filler gel obtained by the implementation of the selection process as defined above.

BRIEF DESCRIPTION OF THE DRAWING FIGURES

The invention may be better understood on reading the following description, and on the examination of the appended drawing, in which.

OSCILLATORY RHEOLOGY MEASUREMENT

The linear viscoelasticity properties of the filler gels may be characterized in oscillatory rheology with a deformation (strain) sweep, via in particular the measurement of their elastic modulus G' (in Pa) and of their phase angle $\delta$(in °).

The elastic modulus G', also known as the "storage modulus", measures the energy returned by the gel when it is subjected to a weak reversible deformation. In a very simplified manner, this quantity may be illustrated by the stiffness of a spring.

The phase angle $\delta$ characterizes the degree of viscoelasticity of a material: it varies between 0° for a 100% elastic material (all the deformation energy is returned by the material, that is to say it regains its initial shape) and 90° for a 100% viscous material (all the deformation energy is lost by the material, that is to say that it flows and completely loses its initial shape). A cutaneous filler gel must be predominantly elastic in order to ensure its filling properties, that is to say that $\delta$ must be preferably less than 45°.

Furthermore, the viscous modulus G", also known as the "loss modulus", may be measured.

The point referred to as the "crossover point" is that where the curves giving G' and G" cross. The stress and deformation strain at this point are those starting from which a material, predominantly elastic at the lower stresses and deformation strains, enters the flow region.

Figure 1:
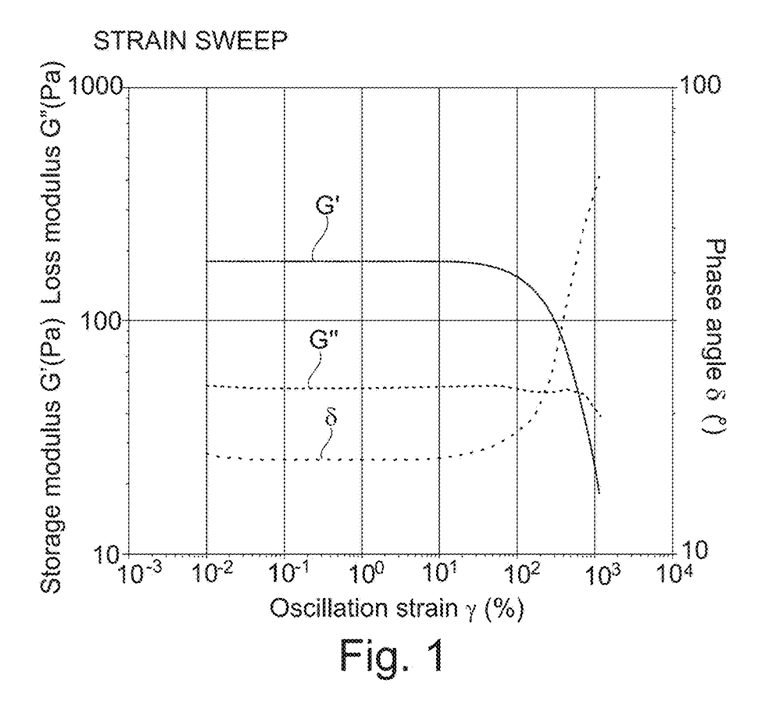
FIG. 1 represents the change in the elastic modulus G' and viscous modulus G" in the case of a deformation (strain) sweep.
Figure 2:
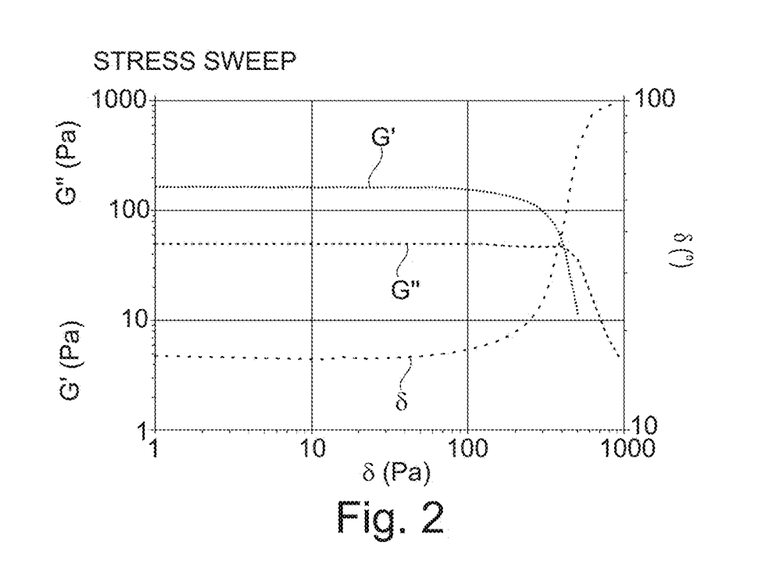
FIG. 2 represents the change in the moduli G' and G" in the case of a stress sweep.

The appearance of the moduli G' and G" and of the phase angle have been represented in FIG. 1 in the case of a deformation strain sweep from 0.01 to 1000% , and in FIG. 2 in the case of a stress sweep from 1 to 1000 Pa.

G' and G" may be measured at 25° C. at the fixed frequency of 1 Hz for example, with a stress or deformation strain sweep using a rheometer.

Use may be made, for example, of the ARES G2 rheometer from TA Instruments, or the Rheostress 6000 rheometer from Thermo Scientific Haake.

Use is made, for example, of a rough upper disc having a diameter of 25 mm, located above and parallel to a rough lower disc having a diameter of 50 mm. The roughness is 500 µm, to avoid any slipping and enables a measurement throughout the volume of the sample, positioned between the discs at a predefined thickness.

The sample is deposited on the lower disc and pressed using the upper disc. The surplus product is removed using a spatula. The temperature is set at 25° C., with an accuracy of 0.5° C.

A bell jar may cover the gel during the measurement, to prevent it from drying out.

Reference may be made to the articles by Magnin, A. and Piau J. M., "Shear Rheometry of Fluids with a Yield Stress", J. Non-Newtonian Fluid Mech. 23, 91 (1987), and Magnin, A. and Piau J. M., "Cone and Plate Rheometry of Yield Stress Fluids. Study of an Aqueous Gel", J. Non-Newtonian Fluid Mech. 36, 85 (1990), regarding the measurement of the elasticity modulus of this type of product.

Of course, the moduli G' and G" may be measured with a different geometry and different apparatus, and different implementation conditions, especially as regards temperature, amount of product deposited and deposition method.

Figure 3:
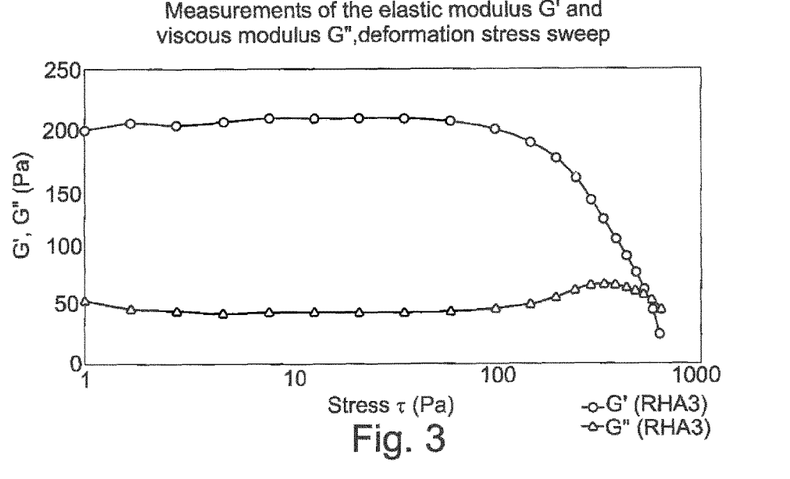
FIG. 3 represents a measurement of the moduli G' and G" in the case of a stress sweep, with a logarithmic scale on the x-axis.
Figure 4:
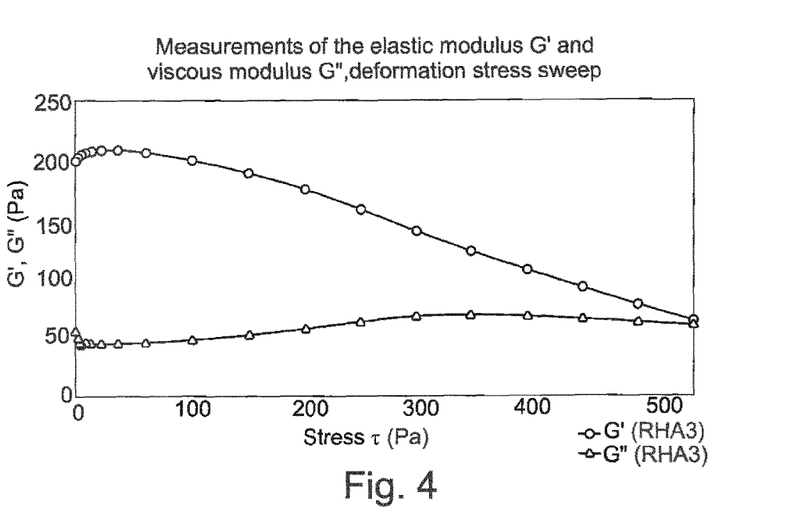
FIG. 4 is a view similar to FIG. 3 with a linear scale on the x-axis.

FIGS. 3 and 4 represent actual measurements for a filler gel RHA3 with respectively logarithmic and linear scales.

G' Integration Score

In accordance with the invention, G' is measured and a G' integration score is calculated.

Figure 5:
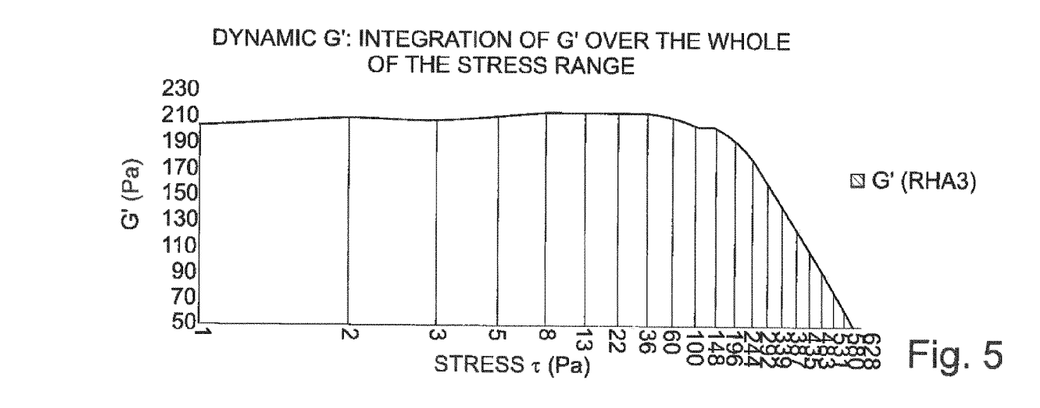
FIGS. 5 and 6 illustrate the calculation of the G' integration score over the whole of the stress range, respectively with the stress and the strain as units on the x-axis.
Figure 6:
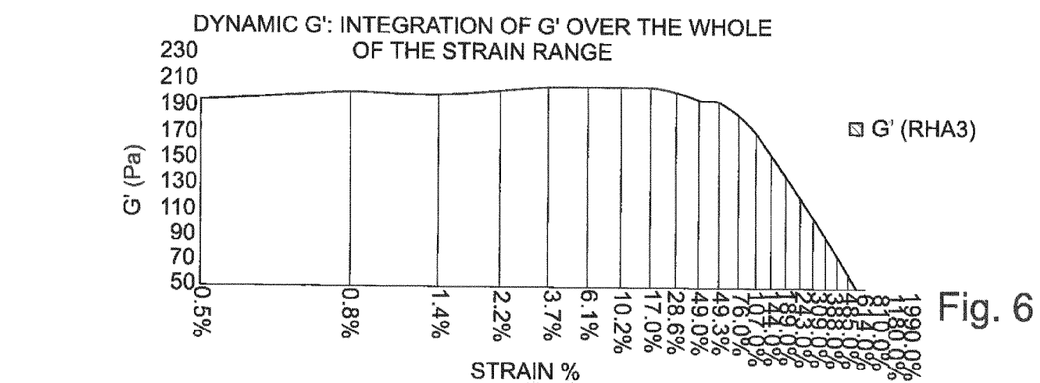

This score corresponds for example to the integration of G' over the whole of the stress range swept, as illustrated in FIG. 5, or over the whole of the deformation strain range, as illustrated in FIG. 6.

It is seen in FIG. 3 that the product RHA3 tested has a modulus G' at the plateau (linear viscoelasticity range) of around 200 Pa.

The same measurement, but represented this time with a linear stress scale (x-axis), makes it possible to see that the decrease of the modulus G' in fact takes place over a wide deformation stress range. There is a crossover point that occurs for a stress close to 600 Pa.

The G' integration score makes it possible to characterize the mechanical performance of the gel, since the result takes into account not only the level of elastic modulus G', but also the width of the plateau, that is to say the width of the deformation or stress range for which the gel is capable of conserving a high modulus G'. This approach thus makes it possible to describe as "resilient" a gel capable of withstanding a wider range of deformation strain or stress.

It is possible to integrate the modulus G' from a low deformation stress, for example 1 Pa, which corresponds to the lower limit, up to the upper limit which may be set in various ways.

It is for example possible to take, as the upper limit, the point where the stress where G' decreases by more than 10% of its value at the plateau, namely, for example, a stress of 150 Pa on the measurement from FIG. 3.

It is also possible to take, as the upper limit, the crossover point, namely around 600 Pa on this measurement. In this case, the integration score also makes it possible to characterize the range of decrease of the modulus G', from the end of the plateau to the crossover.

Although the result of the calculation is different depending on the upper limit chosen, a comparison between gels may be carried out provided that the same configuration for measuring and calculating the score (same lower and upper limits) is stayed within for the products compared. The upper limit must in any case lie beyond the linear viscoelasticity range, that is to say after the plateau, when G' decreases.

The calculation is illustrated in FIGS. 5 and 6, depending on whether the sweep is a stress sweep, which results in a score in $Pa^2$, or a deformation strain sweep, which results in a score in Pa.

In the example considered, the product RHA3 is a product having strong enough mechanical properties to support indications such as the filling of deep wrinkles of the face.

Knowledge of the integration score proves to constitute an invaluable tool for the comparison between products.

Figure 7:
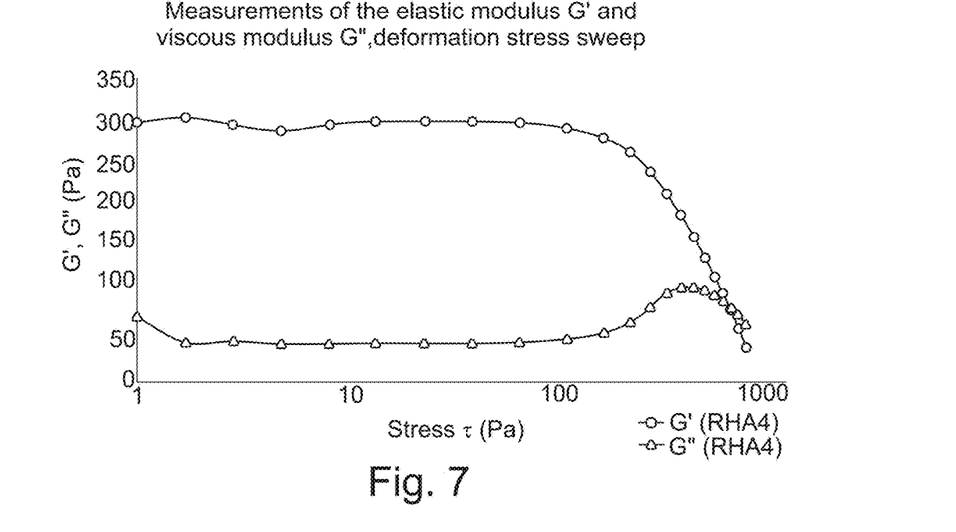
FIG. 7 is a view similar to FIG. 3 for another gel measured.

By way of illustration, a product RHA4 was tested and the values of G' and G" are given in FIG. 7, in the case of a stress sweep.

This product RHA4 belongs to the same range as the product RHA3, these two products resulting from similar manufacturing processes. But RHA4 is a "volumizing" product, i.e. that has mechanical properties even better than those of RHA3, for supporting indications such as the filling of the deepest wrinkles and/or partially atrophied regions of the face.

In FIG. 7, it is seen that the product RHA4 tested has a modulus G' at the plateau of around 300 Pa, and a crossover that occurs for a stress close to 600 Pa.

Figure 8:
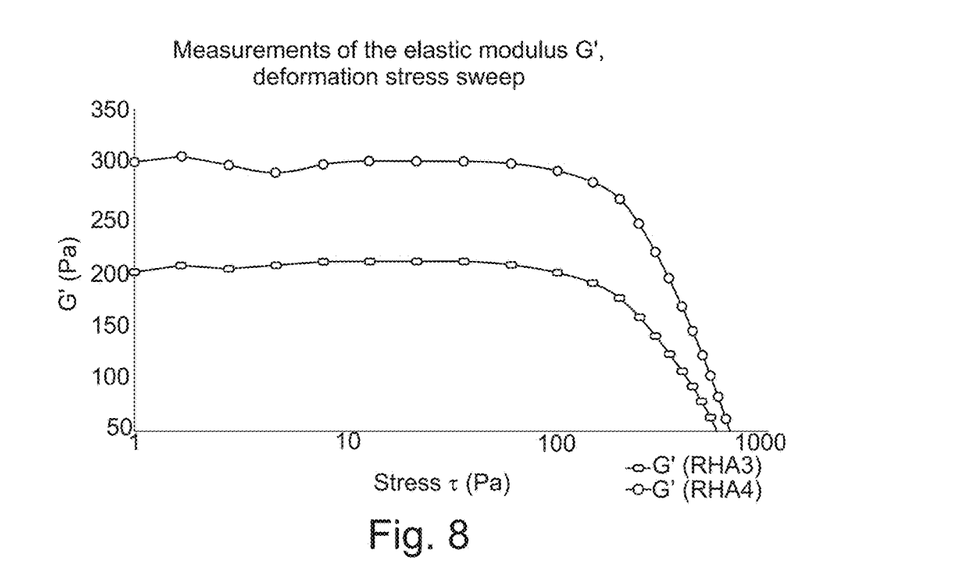
FIGS. 8 and 9 compare the changes in the elasticity modulus G' for various filler gels.

It is seen in FIG. 8 that the difference between the two products RHA3 and RHA4 is observed directly by the value of G', knowing that the stress crossovers are similar for these two products.

The calculation of the G' integration score for the two products RHA3 and RHA4 makes it possible to conclude that RHA4 has a greater mechanical power in comparison with RHA3, in agreement with the respective indications of these two products.

Figure 9:
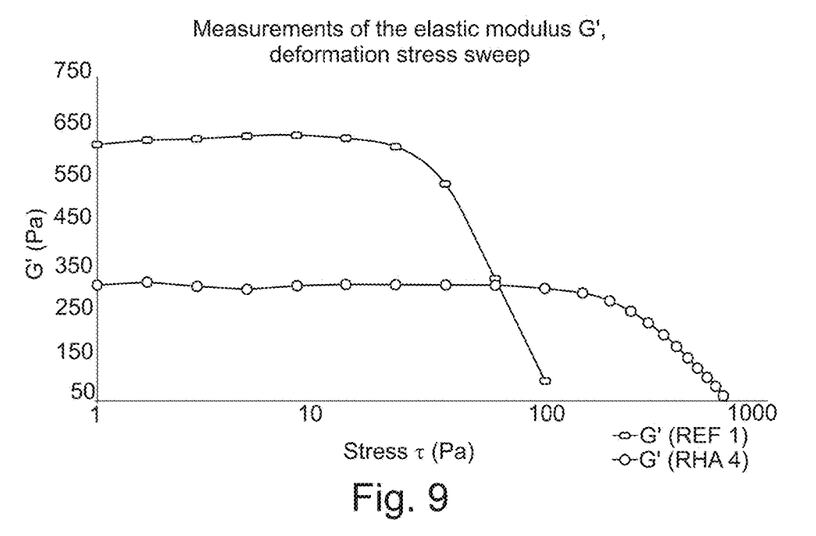

Nevertheless, the comparison becomes less intuitive when the products compared have very different plateau widths (linear viscoelasticity ranges), as illustrated in FIG. 9, where the moduli G' of the products RHA4 and REF1 have been represented.

The product REF1 has indications similar to those of RHA3. This implant has a very high level of the modulus G', greater even than that of the gel RHA4. A rheological assessment that is based only on the value of the modulus G' would lead to the conclusion that the gel REF1 is a stronger product than the gels RHA3 and RHA4. However, this is data that is contradicted by experimentation and the "sensory" assessment of these products, in particular by a test of pressing the gels between two fingers.

Figure 10:
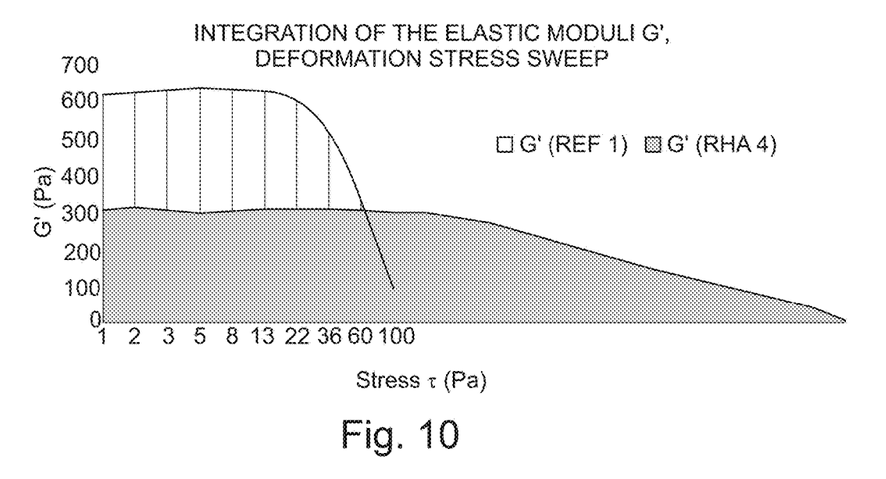
FIG. 10 illustrates the calculation of the integration scores in the case of the gels from FIG. 9.

The calculation of the G' integration score gives information that agrees with the sensory assessment. In fact, it is seen in FIG. 10 that REF1 also has a shorter linear viscoelasticity range, which reduces its mechanical resilience, as quantified by the integration of the modulus G'.

Figure 11:
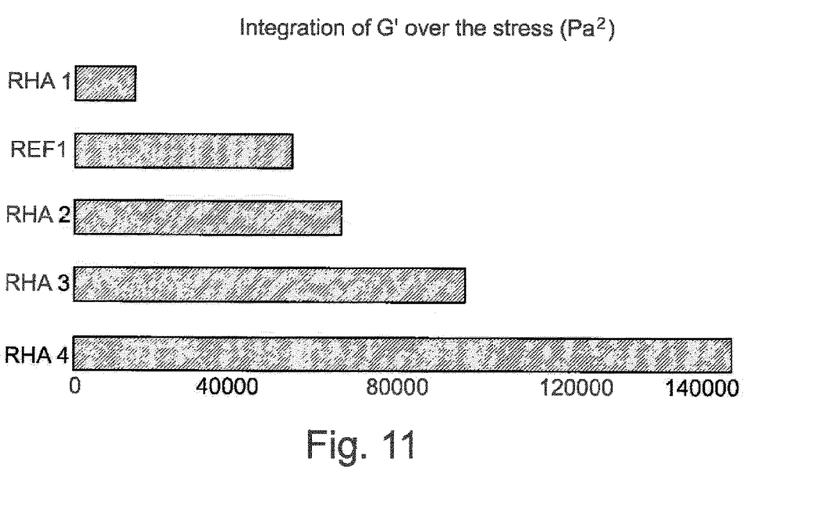
FIG. 11 compares G' integration scores of various gels.

FIG. 11 demonstrates the contribution of the invention in terms of selection and differentiation of the mechanical properties for several products. In a simplified manner, the gel RHA1, having a relatively low score (of the order of $10^4$), is indicated for superficial wrinkles and the thinnest regions of the face, and the gel RHA2 is indicated for moderate and fine facial wrinkles. The products RHA3 and REF1 are indicated for deep facial wrinkles, and the product RHA4, the G' integration score of which is the highest (more than $10^5$) is indicated for the deepest wrinkles and/or the partially atrophied regions of the face.

The calculation of the G' integration score over the stress or the deformation strain, in oscillatory rheology, as presented above, gives information on the width of the linear viscoelasticity range, which thus expresses the "toughness" of the crosslinked hyaluronic acid network and the mechanical resilience of the implant.

But as soon as the modulus G' decreases, the end of the horizontal plateau in the oscillatory rheology curves, and in particular beyond the crossover point, the viscoelasticity regime is no longer linear. In other words, starting from a certain level of applied stress and/or deformation strain, the hyaluronic acid (HA) network no longer adapts to the state of stress it is subjected to, and the elastic modulus G' decreases as there is this entanglement of the HA chains.

Thus, oscillatory rheology is well suited for obtaining information on the characterization of the polymer network (length of the chains, degree of crosslinking, concentration), but the data at the plateau only correspond to the simplest (linear) viscoelasticity, observed for small deformation strains.

On the other hand, the shaping of the implant and its behaviour under deformation no longer come under linear viscoelasticity, but on the contrary a non-linear regime that is more difficult to characterize. Thus, oscillatory rheology does not always make it possible to properly evaluate "what happens" beyond the linear regime, and particularly after the crossover point.

Measurement of the creep makes it possible to evaluate the behaviour of the gel in a non-linear regime, where it is subjected to a continuous stress in the same direction. In other words, it is a deformation forced by the application of a continuous stress which causes the gel to creep.

Measurement of the creep gives information on the ability of the gel to deform under a significant stress. However, it is important for an implant to be able to be injected easily through a fine needle, to be positioned correctly in the injection site and according to the stresses applied by the practitioner, and to adapt to the stresses and to the dynamics of the face, so as to give the effect of natural filling.

The situation is summarized in the table below:

| | Types of measurement | |
| --- | --- | --- |
| | Oscillatory rheology measurement | Creep measurement |
| Quantities usually associated | G', crossover, δ (small deformations, linear viscoelasticity) | Immediate/delayed elastic deformations, viscous deformations (broad and irreversible deformations, non-linear viscoelasticity) |
| Use within the context of the invention | The integration of the modulus G' makes it possible to obtain an indication of mechanical resilience, i.e. the ability of the gel to maintain its structure over a broad stress range | The greater the slope of the creep, the more easily deformable/malleable the gel is, in the situation of shaping via an imposed stress (e.g. modelling of the practitioner, facial movements to which the gel must adapt) |

Creep Measurement

Figure 12:
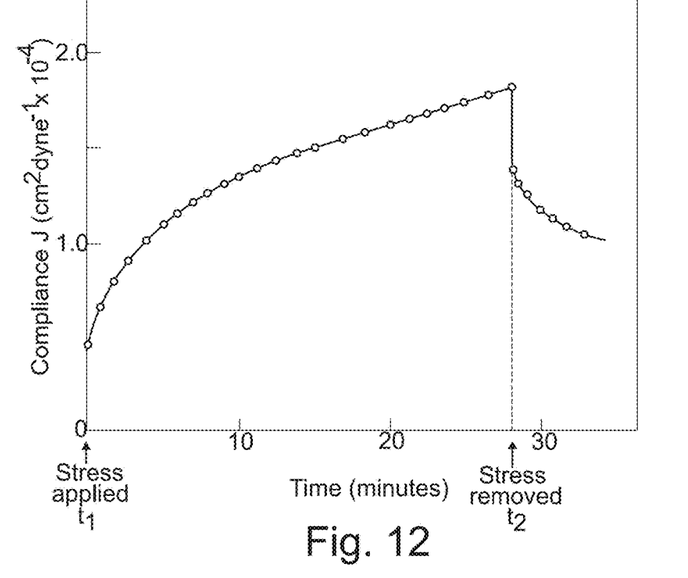
FIG. 12 illustrates the principle of a creep measurement.

A constant and continuous stress is applied to the gel (unlike the measurement of G' and G" where the stress is oscillating) over a given time, and its reaction (deformation) is measured. The typical type of curve obtained is such as represented in FIG. 12.

The fixed stress is applied between t1 and t2, and the elastic compliance J in $Pa^{-1}$ as a function of the time is measured. It is also possible to measure the deformation, which gives the same type of curve.

After an instantaneous and delayed elastic deformation region, a straight line is observed, the slope of which may be measured. The slope is even greater when the gel creeps easily.

In order to measure the creep, it is possible to use the same equipment as for measuring the moduli G' and G", but operating the rheometer in "creep" (and not oscillating) mode.

For the measurements, a constant stress of 5 Pa for example is applied, over at least 300 s (preferably 450 s).

The slope of the creep is expressed preferably in $s^{-1}$, as the ratio between imposed stress σ(3 (Pa) and viscosity η(Pa·s): σ/η.

For a hyaluronic acid implant, gels of high resilience (i.e. having a high G' integration score) may be expected to also be less malleable gels, i.e. gels that are less disposed to creep.

This is true in a general manner, that is to say that in a same range of products, or for various HA implants having very different indications, the products having a high G' integration score generally have a slope of the creep that is lower than that of products having a lower G' integration score.

But the measurement of the creep makes it possible to differentiate products for which the G' integration scores are similar.

Thus, two products having substantially the same "mechanical resilience or power" (linked to the G' integration score), will generally have filling performances and resistance to degradation performances which are quite similar.

On the other hand, the product that has a significantly higher slope of the creep will have the advantage of being more easily injectable or malleable. This is an impression which is confirmed by the practitioners during the use of such products. The patients also describe a more natural effect, and the reduction, or even the absence, of discomfort after the injection session.

The combination of the calculation of the integration score and of the slope of the creep therefore gives information, in an overall and thorough manner, on the behaviour of the gel, both on its behaviour "in place" or in situ (durability, strength of the gel, firmness and mechanical power), and on its behaviour in a shaping situation (placement of the product during injection, deformation forced by the dynamics of the face, natural effect).

It is thus possible to select "2-in-1" products that bring together two a priori antinomic features, namely both a high resilience (the gels are capable of maintaining their structure and their function despite the stresses undergone) and a good malleability for an optimal and natural shaping of the implant, and for following the dynamics of the face. This selection may be made without in situ tests.

EXAMPLE 1

Figure 13:
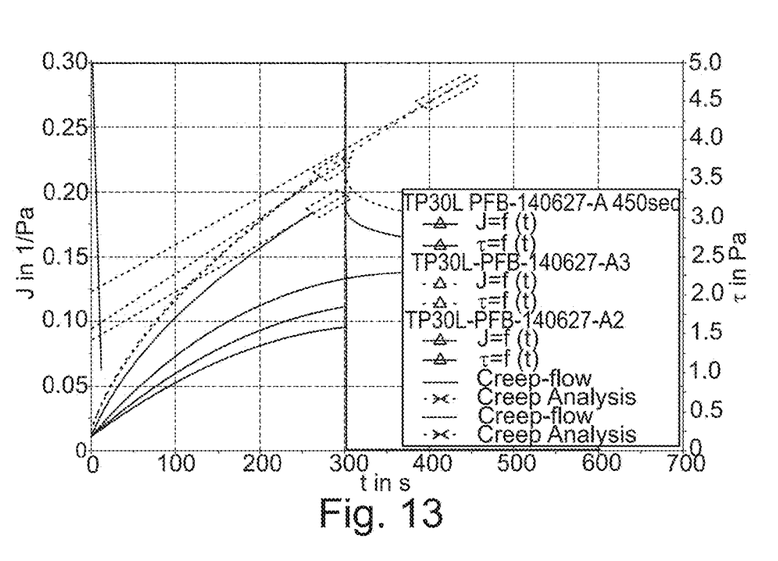
FIG. 13 represents examples of creep me measurements.

Three measurements were carried out using 3 samples from a same batch of gel RHA2, namely two measurements with a creep over 300 s, and one measurement with creep over 450 s. The results are reported in FIG. 13.

The slope of the creep is calculated in the table below for the three measurements:

| Sample | Creep time at 5 Pa | Slope of the creep (×5 $s^{-1}$) |
| --- | --- | --- |
| A | 450 s | 3.7 × $10^{-4}$ |
| A2 | 300 s | 3.8 × $10^{-4}$ |
| A3 | 300 s | 4.3 × $10^{-4}$ |

Although the results regarding these three samples of a same gel do not exhibit perfectly identical slopes, the three results nevertheless remain within the same order of magnitude, and the differences observed are not in fact significant with respect to the differences that may exist regarding different gels (see the following examples). The slope is not modified either between 300 and 450 s of creep; the latter configuration makes it possible on the other hand to obtain the slope over a longer interval, rendering the measurement more reliable. In order to prevent the gel from drying out during the measurement, the use of a bell jar over the measurement plate is recommended.

EXAMPLE 2

Regarding the four gels RHA1, RHA2, RHA3 and RHA4, the creep is determined at 5 Pa over 300 s.

The results of the calculation of the slope of the creep are the following for the four products:

| Sample | Slope of the creep (×5 $s^{-1}$) |
| --- | --- |
| RHA4 | 2.2 × $10^{-5}$ |
| RHA3 | 4.9 × $10^{-5}$ |
| RHA2 | 3.8 × $10^{-4}$ |
| RHA1 | 1.5 × $10^{-3}$ |

Figure 14:
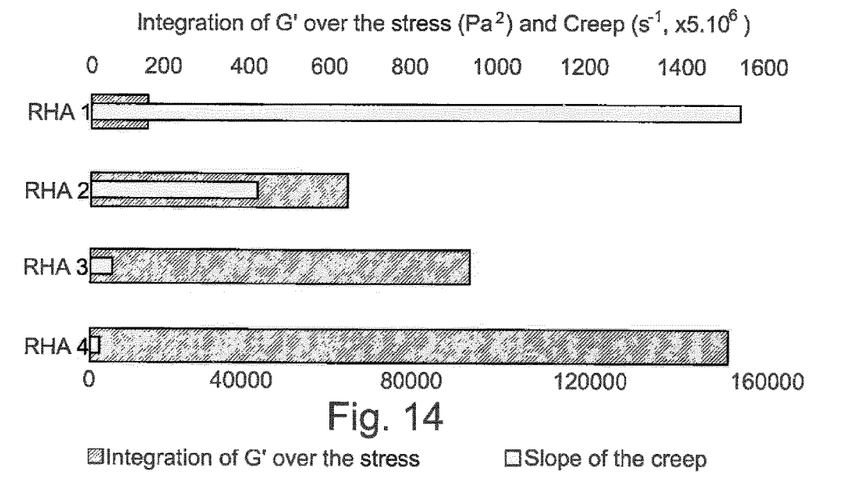
FIGS. 14 and 15 compare the G' integration scores lower scale and the slopes of the creep upon scale for various filler gels tested.

The representation of these results, as illustrated in FIG. 14, in combination with the modulus G' integration score, exhibits a reverse order between the products over these two scales (slope of the creep represented ×5 $10^6$ for a better graphical representation).

EXAMPLE 3

Similar measurements were carried out between other products REF2 to REF4 and RHA4, which are gels with similar G' integration scores.

The products RHA2, REF2, REF4 and REF3 are cross-linked HA implants, indications of which are similar (injections into the middle dermis of the face).

Figure 15:
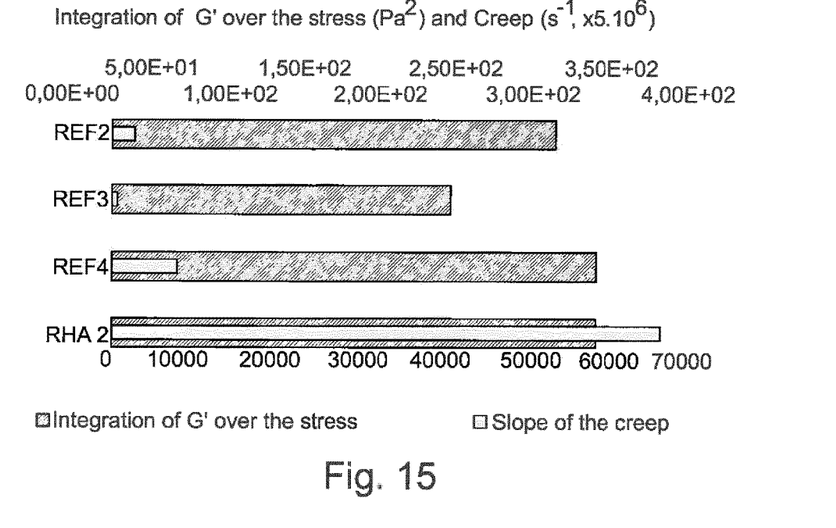

The combined results of these products, represented in FIG. 15, exhibit:

relatively similar G' integration scores, reflecting a same category of products (in the range 40 000-60 000 $Pa^2$), significant differences between the slopes of the creep. In particular, the product RHA2 has a much higher slope of the creep than the other products. This result corroborates the opinion of the practitioners who test this product, describing it as easy to position, flexible and integrating perfectly into the tissues at the injection zone (but without migrating), and giving a natural effect. The persistence performance of this product is nevertheless not affected (which is in agreement with the G' integration score), the clinical studies in progress describing an effect is still visible (significant) twelve months after the injection of this product.

The invention is not limited to the examples which have just been described. In particular it is found to apply to other gels to be implanted into human tissues.

The expression "having a" should be understood as being synonymous with "comprising at least one".

The invention claimed is:

1. A method for selecting one or more filler gel(s) for its(their) resilience properties among a plurality of filler gels through evaluation of their mechanical performance(s), said method comprising:

subjecting a sample of each filler gel to oscillating stress and deformation strains using a rheometer and a rheometer control unit having computational means;

determining elastic modulus G' of each filler gel within a stress and/or deformation strain interval until beyond a linear viscoelasticity plateau;

delivering a G' integration score of each filler gel representative of integration of G' over the stress and/or deformation strain within a stress and/or deformation strain interval that includes values of the modulus G' encountered beyond the linear viscoelasticity plateau;

comparing said G' integration score(s) of each filler gels; and selecting the one or more filler gel(s) that exhibits(s) the higher G' integration score for application in a selected treatment regimen.

2. The method according to claim 1, wherein the integration is a single integration and is carried out over the stress.

3. The method according to claim 1, wherein the integration is a single integration and is carried out over the strain.

4. The method according to claim 1, wherein the integration being a double integration and being carried out over the stress and the strain.

5. The method according to claim 1, wherein the integration interval have as upper limit the deformation strain and/or stress values taken at the crossover point.

6. The method according to claim 1, further comprising an information representative of said score printed or displayed on an information medium.

7. The method of claim 6, wherein the information medium is a notice, a packaging of the gel, an information or advertising panel, a commercial or medical brochure, or a television screen or mobile telephone screen.

8. The method according to claim 1, wherein a creep measurement is used to differentiate gels for which the G' integration scores are similar.

* * * * *